United States Patent
Chen et al.

(10) Patent No.: US 12,314,809 B2
(45) Date of Patent: May 27, 2025

(54) ANTI-COUNTERFEIT POLYNUCLEOTIDE TAGGANTS

(71) Applicant: MICROSOFT TECHNOLOGY LICENSING, LLC, Redmond, WA (US)

(72) Inventors: Yuan-Jyue Chen, Seattle, WA (US); Karin Strauss, Seattle, WA (US); Christian Paquin, Herndon, VA (US); Alexander Steven Crown, Bellevue, WA (US); Sergey Yekhanin, Redmond, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 0 days.

(21) Appl. No.: 18/301,455

(22) Filed: Apr. 17, 2023

(65) Prior Publication Data

US 2024/0346270 A1    Oct. 17, 2024

(51) Int. Cl.
   *G06K 7/14*     (2006.01)
   *C12Q 1/6823*   (2018.01)
   *G16B 50/30*    (2019.01)

(52) U.S. Cl.
   CPC ......... *G06K 7/1413* (2013.01); *C12Q 1/6823* (2013.01); *G16B 50/30* (2019.02)

(58) Field of Classification Search
   CPC .. G06K 7/1413; C12Q 1/6823; C12Q 1/6834; G16B 50/30
   See application file for complete search history.

(56) References Cited

U.S. PATENT DOCUMENTS

2005/0026181 A1   2/2005   Davis
2023/0101083 A1   3/2023   Chen
                  (Continued)

FOREIGN PATENT DOCUMENTS

WO   2018057502 A2   3/2018
WO   2019183359 A1   9/2019

OTHER PUBLICATIONS

"Notes on Digital Coding", In Proceedings of IEEE, vol. 37, Jun. 1949, pp. 657.
(Continued)

*Primary Examiner* — Jamara A Franklin
(74) *Attorney, Agent, or Firm* — Newport IP, LLC; Benjamin A. Keim

(57) ABSTRACT

Molecular anti-counterfeiting taggants are made from a plurality of synthetic polynucleotides that collectively encode a bit sequence using the sequences and hybridization states of the polynucleotides. The polynucleotide taggant is placed on an item as a molecular identifier of authenticity. The bit sequence encoded by the polynucleotide taggant is read out using a substrate which has bound polynucleotides complexes that hybridize with the synthetic polynucleotides in the polynucleotide taggant. A detectable signal is present where hybridization occurs. To prevent a bad actor from reverse engineering and creating a copy of the polynucleotide taggant using the results of hybridization to the substrate, multiple versions of the substrate are created. Each version hybridizes to different subsets of the synthetic polynucleotides in the polynucleotide taggant. A detectable pattern on the substrate that is present when exposed to the polynucleotide taggant is used for validating authenticity of the item.

20 Claims, 8 Drawing Sheets

(56) References Cited

U.S. PATENT DOCUMENTS

| | | |
|---|---|---|
| 2023/0125457 A1 | 4/2023 | Yuan-Jyue |
| 2023/0313276 A1 | 10/2023 | Chen et al. |
| 2024/0369476 A1 | 11/2024 | Yuan-Jyue |

OTHER PUBLICATIONS

Bloch, et al., "Labeling Milk Along Its Production Chain with DNA Encapsulated in Silica", In Journal of Agricultural and Food Chemistry, vol. 62, Issue 43, Oct. 8, 2014, pp. 10615-10620.

Ding, et al., "Identifying Exogenous DNA in Liquid Foods by Gold Nanoparticles: Potential Applications in Traceability", In Journal of ACS Food Science & Technology, vol. 1, Issue 4, Apr. 13, 2021, pp. 605-613.

Dirks, et al., "Paradigms for Computational Nucleic Acid Design", In Journal of Nucleic Acids Research, vol. 32, Issue 4, Feb. 27, 2004, pp. 1392-1403.

Doroschak, et al., "Rapid and Robust Assembly and Decoding of Molecular Tags with DNA-Based Nanopore Signatures", In Journal of Nature Communications, vol. 11, Issue 1, Nov. 2020, pp. 1-8.

Galimberti, et al., "DNA Barcoding as a New Tool for Food Traceability", In Journal of Food Research International, vol. 50, Issue 1, Jan. 1, 2013, pp. 55-63.

Goodwin, et al., "Coming of Age: Ten Years of Next-Generation Sequencing Technologies", In Journal of Nature Reviews Genetics, vol. 17, Issue 6, Jun. 2016, pp. 333-351.

Jonas, et al., "Safety Considerations of DNA in Food", In Journal of Annals of Nutrition and Metabolism, vol. 45, Issue 6, 2001, pp. 235-254.

Kanagawa, Takahiro, "Bias and Artifacts in Multitemplate Polymerase Chain Reactions (PCR)", In Journal of Bioscience and Bioengineering, vol. 96, Issue 4, Jan. 1, 2003, pp. 317-323.

Koch, et al., "A DNA-of-things Storage Architecture to Create Materials with Embedded Memory", In Journal of Nature Biotechnology, vol. 38, Issue 1, Jan. 2020, pp. 39-43.

Kosuri, et al., "Large-scale De Novo DNA Synthesis: Technologies and Applications", In Journal of Nature Methods, vol. 11, Issue 5, May 2014, pp. 499-507.

Lu, et al., "Fabrication and Characterization of Paper-Based Microfluidics Prepared in Nitrocellulose Membrane by Wax Printing", In Journal of Analytical Chemistry, vol. 82, Issue 1, Jan. 2010, pp. 329-335.

Mikutis, et al., "Silica-Encapsulated DNA-Based Tracers for Aquifer Characterization", In Journal of Environmental Science & Technology, vol. 52, Issue 21, Oct. 2, 2018, pp. 12142-12152.

Mora, et al., "Ultrasensitive Quantification of Pesticide Contamination and Drift using Silica Particles with Encapsulated DNA", In Journal of Environmental Science & Technology Letters, vol. 3, Issue 1, Jan. 12, 2016, pp. 19-23.

Nilsson, et al., "Evaluation of Different Cleaning Strategies for Removal of Contaminating DNA Molecules", In Journal of Genes, vol. 13, Issue 1, Jan. 17, 2022, pp. 1-9.

Oss, et al., "Mechanism of DNA (Southern) and Protein (Western) Blotting on Cellulose Nitrate and Other Membranes", In Journal of Chromatography, vol. 391, Jan. 1, 1987, pp. 53-65.

Paunescu, et al., "Protection and Deprotection of DNA—High-Temperature Stability of Nucleic Acid Barcodes for Polymer Labeling", In Journal of Angewandte Chemie, vol. 15, Issue 52, Mar. 6, 2013, pp. 4269-4272.

"International Search Report and Written Opinion Issued in PCT Application No. PCT/US2023/012878", Mailed Date: May 8, 2023, 10 Pages.

Puddu, et al., "Magnetically Recoverable, Thermostable, Hydrophobic DNA/Silica Encapsulates and Their Application as Invisible Oil Tags", In Journal of ACS Nano, vol. 8, Issue 3, Feb. 25, 2014, pp. 2677-2685.

Qian, et al., "Barcoded Microbial System for High-Resolution Object Provenance", In Journal of Science, vol. 368, Issue 6495, Jun. 2020, pp. 1135-1140.

Trevino, et al., "DNA Microarrays: a Powerful Genomic Tool for Biomedical and Clinical Research", In Journal of Molecular Medicine, vol. 13, Issue 9, Sep. 2007, pp. 527-541.

Vasisht, et al., "FarmBeats: An IoT Platform for Data-Driven Agriculture", In Proceedings of 14th USENIX Symposium on Networked Systems Design and Implementation, Mar. 27, 2017, pp. 515-529.

Wang, et al., "Nanopore Sequencing Technology, Bioinformatics and Applications", In Journal of Nature Biotechnology, vol. 39, Issue 11, Nov. 2021, pp. 1348-1365.

Wolfe, et al., "Sequence Design for a Test Tube of Interacting Nucleic Acid Strands", In Journal of ACS Synthetic Biology, vol. 4, Issue 10, Oct. 16, 2015, pp. 1086-1100.

Xu, et al., "Design of 240,000 Orthogonal 25mer DNA Barcode Probes", In Journal Proceedings of the National Academy of Sciences, vol. 106, Issue 7, Feb. 17, 2009, pp. 2289-2294.

Zhang, et al., "Dynamic DNA Nanotechnology using Strand-Displacement Reactions", In Journal of Nature Chemistry, vol. 3, Issue 2, Feb. 2011, pp. 103-113.

Berk, et al., "Rapid Visual Authentication Based on DNA Strand Displacement", In Journal of ACS Applied Materials & Interfaces, vol. 13, Issue 16, Apr. 14, 2021, pp. 19476-19486.

Kautz, et al., "Nonrandom binary superimposed codes", In Journal of IEEE Transactions on Information Theory vol. 10, Issue 4, Oct. 1964, pp. 363-377.

Berk, et al., "Rapid Visual Authentication Based on DNA Strand Displacement," ACS Applied Materials & Interfaces, Apr. 14, 2021, pp. 19476-19486.

International Search Report and Written Opinion received for PCT Application No. PCT/US2024/023478, Jul. 15, 2024, 13 pages.

International Search Report and Written Opinion received for PCT Application No. PCT/US2024/025891, Aug. 9, 2024, 09 pages.

DATAWORD 500     GENERATOR MATRIX 502     BIT SEQUENCE / CODEWORD 300 k bits     m     m bits

BIT POSITION 302                    BIT SUBSET 504

SELECT SUBSET OF BITS

ANTI-COUNTERFEIT POLYNUCLEOTIDE TAGGANTS

BACKGROUND

Forgeries and counterfeits are problems in many industries and for many types of valuable items such as artwork, jewelry, wine, foods, and designer brands. Identifying a forgery or counterfeit item can be challenging because a typical purchaser may not be able to distinguish a fake item from an authentic item. One solution is to use anti-counterfeit taggants as a marker to identify authentic items. Absence of an anti-counterfeit taggant or an incorrect taggant may indicate an inauthentic item. Holographic stickers, radio-frequency identification (RFID) tags, and quick response (QR) codes are all used as anti-counterfeit taggants. Even molecules such as deoxyribonucleic acid (DNA) have been proposed as possible taggants.

However, many types of anti-counterfeit taggants can themselves be forged by sophisticated bad actors. One type of attack is simply copying the taggant. This can be done relatively easily for QR codes and is still possible, yet more difficult, with holographic stickers and RFID tags. Even DNA tags can be copied if the bad actor has sufficient molecular biology skills to sequence a DNA taggant and synthesize new molecules with the same sequence. Increasingly complex and exotic types of taggants make counterfeiting the taggants themselves more difficult. However, bad actors can respond by developing ever more sophisticated attacks. Accordingly, it is desirable to develop new types of taggants that are more difficult for a bad actor to copy. The following disclosure is made with respect to these and other considerations.

SUMMARY

This disclosure provides techniques and systems that use polynucleotides as anti-counterfeit taggants. The polynucleotide taggants use a combination of nucleotide sequences and a hybridization state between strands of polynucleotides to encode a bit sequence. That bit sequence, a string of 0s and 1s, functions as an identifier that provides strong forgery protection. A polynucleotide taggant includes many synthetic polynucleotides. The synthetic polynucleotides include barcode strands that have a portion, called a unique barcode domain, which encodes a position in the bit sequence. For example, the sequence of a unique barcode domain can encode that a given synthetic polynucleotide represents the eighth bit (e.g., the 1 in the string 0000 0001 00) of a bit sequence. The presence or absence of another synthetic polynucleotide, called a blocker strand, hybridized to the barcode strand encodes the bit value. The absence of a blocker strand can indicate the bit value of 1 while the presence indicates the bit value of 0 or vice a versa.

The bit sequence encoded by a polynucleotide taggant is read out by the use of a substrate coated with bound polynucleotide complexes at specific assay locations. The substrate could be, for example, a nitrocellulose membrane. Barcode strands that are not hybridized to a blocker strand will hybridize to one of the bound polynucleotide complexes. The presence of a blocker strand prevents hybridization and so barcode strands that are hybridized to a blocker strand will not hybridize to the polynucleotides attached to the surface of the substrate. The pattern of hybridization, which locations are hybridized to a barcode strand, can be detected. One way of doing this is by attaching fluorescent molecules to the polynucleotides so that hybridization with the bound polynucleotide complexes can be visually detected. The pattern of hybridization on a substrate, whether detected by fluorescence or other means, is interpreted to identify specific bit values (i.e., 0 or 1) as well as the order of the bits. The bit sequence can then be determined based on the pattern of hybridization.

This type of polynucleotide taggant is designed to thwart a particular attack. Specifically, using hybridization states rather than nucleotide sequences alone to encode information prevents a bad actor from re-creating the polynucleotide taggants by sequencing and synthesis. Sequencing will require separating hybridized strands, typically by heating as a step in polymerase chain reaction (PCR), in which the hybridization state is lost. Successful sequencing will identify the sequences of all the barcode strands and blocker strands in the polynucleotide taggant. However, without knowing which barcode strands were hybridized to a blocker strand the original bit sequence cannot be recovered.

There is yet a more sophisticated potential attack that could be employed by a bad actor that has both a sample of the polynucleotide taggant and the substrate used to read out the bit sequence. A sophisticated attacker could use the following steps to identify the bit sequence encoded by a polynucleotide taggant. (1) Take a sample of the taggant (sample A). (2) Take a sample of a wash after the taggant is applied to the substrate (sample B). Sample B should contain all of the barcode strands hybridized to blocker strands because these will not have hybridized to the polynucleotides on the substrate. (3) Dehybridize polynucleotides that have hybridized to the bound polynucleotide complexes on the substrate and take a sample (sample C). (4) Sequence each sample separately. (5) By comparing what is present in sample A that has disappeared or been reduced in C it will be possible to identify the initial hybridization conditions. Meaning that it is possible to identify which of the barcode strands were hybridized to a blocker strand thereby identifying which bit values are 1 bits and 0 bits.

This disclosure provides a solution to prevent the more sophisticated attack that could be implemented if the bad actor were to use the substrate to deduce the initial hybridization states as described above. Specifically, any given substrate is designed to only read a portion of the bit sequence encoded by the polynucleotide taggant. Thus, even if a bad actor uses one substrate to determine the hybridization states, and thus bit values, he or she would only be able to do so for a subset of the bit values encoded by the polynucleotide taggant. For example, a collection of synthetic polynucleotides that make up a polynucleotide taggant may encode 25 bits. However, any given substrate will read out the values of only 9 bits. Thus, any given substrate only detects a subset of the bits encoded by the polynucleotide taggant.

If, however, all of the substrates detected the same 9 bits, for example, the other bits encoded by the polynucleotide taggant would be superfluous and the bad actor would be able to employ the same attack. This is prevented by using multiple versions of the substrate each prepared with different bound polynucleotide complexes attached to the assay locations. The sequences of the bound polynucleotide complexes determine which bit from the sequence of bits is detected at that assay location. Thus, there will be multiple substrates that each detect a different subset of bits. If the bad actor creates a counterfeit polynucleotide taggant based on the bits detected by one version of the substrate and applies those polynucleotides to a counterfeit item, the counterfeit taggant will not generate the correct pattern when checked with a different version of the substrate.

The combinatorial possibilities allow for a large number of different versions of the substrate. The bad actor cannot create a counterfeit polynucleotide taggant with the correct hybridization states unless he or she is able to obtain versions of the substrate that detect each bit in the bit sequence encoded by the polynucleotide taggant. The bad actor will likely not know how many total bits are encoded by the polynucleotide taggant nor will he or she be able to readily obtain every version of the substrate. Thus, it becomes highly unlikely that the bad actor will be able to successfully reverse engineer the hybridization state of the original polynucleotide taggant even if he or she has access to one or more versions of the substrate.

The system also includes a computing device that determines if the pattern detected from a given substrate is the correct pattern that would be generated by a valid polynucleotide taggant. The computing device uses a validation code associated with the substrate to identify which detected pattern is the correct pattern for that substrate. The validation code may be, for example, a barcode or QR code placed on the substrate. The correct pattern will be different for different versions of the substrate. This second factor is used by the computing device to correlate a specific pattern (e.g., a pattern of fluorescence) with the substrate. If the correct pattern is detected, the computing device can identify an item tagged with the polynucleotide taggant as authentic. If not, it may return an error or indication of inauthenticity. Because there are different versions of the substrate, even if the bad actor creates a counterfeit polynucleotide taggant that yields the correct result with one version of the substrate it will not do so with a different version. The use of multiple different versions of a substrate can defeat sophisticated attacks to create counterfeit polynucleotide taggants.

This Summary is provided to introduce a selection of concepts in a simplified form that are further described below in the Detailed Description. This Summary is not intended to identify key features or essential features of the claimed subject matter nor is it intended to be used to limit the scope of the claimed subject matter. The term "techniques," for instance, may refer to system(s) and/or method (s) as permitted by the context described above and throughout the document.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items. The figures are schematic representations and items shown in the figures are not necessarily to scale.

DETAILED DESCRIPTION

Figure 1A:
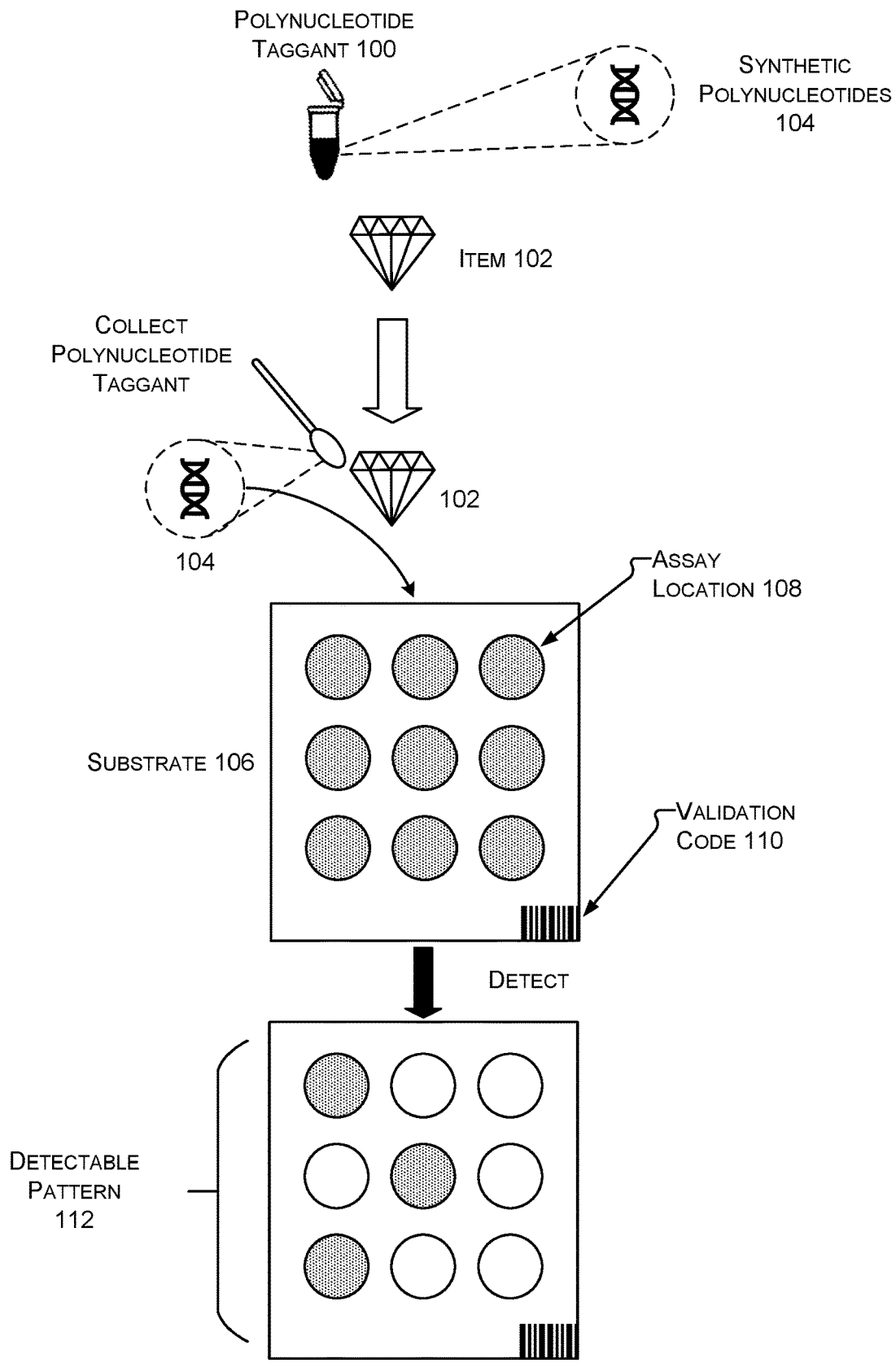
FIGS. 1A and 1B illustrate the use of a polynucleotide taggant to tag an item and use of a pattern created on a substrate to validate the authenticity of the item.

Taggants are a physical or chemical marker added to materials for tracking and authentication. They can be utilized to differentiate authentic products from counterfeits and identify IDs for traceability purposes. Polynucleotide, or DNA. Taggants (tags) are a unique solution for this application because of their nano-size, non-toxicity, and programmability. Nucleic acids have been previously used as anti-counterfeit tags as described in U.S. Pat. No. 5,451,505. However, the '505 patent and other previous work discussing polynucleotide tags use the sequence of one or a few polynucleotides as the tag. Due to advances in polynucleotide synthesis and sequencing technology, simple polynucleotide tags are vulnerable to read and rewrite attacks (i.e., sequencing and synthesis). More sophisticated techniques that use polynucleotides as anti-counterfeit tags are discussed in U.S. Pat. Pub. No. 2023/0101409 filed on Sep. 30, 2021, and U.S. Pat. Pub. No. 2023/0101083 filed on Sep. 30, 2021. These techniques require sequencing to read out the tags which requires expensive and specialized equipment. Techniques for using hybridization state as well as nucleotide sequences to create an anti-counterfeit tag that can be read using a pattern of fluorescence without sequencing are described in U.S. Pat. Pub. No. US 2023/0313276 filed on Mar. 29, 2022. The anti-counterfeit polynucleotide taggants of this disclosure are based on the technology introduced in the '276 publication.

Polynucleotides as used herein include both deoxyribonucleic acid (DNA), ribonucleic acid (RNA), and hybrids containing mixtures of DNA and RNA. DNA and RNA include nucleotides with one of the four natural bases cytosine (C), guanine (G), adenine (A), thymine (T), or uracil (U) as well as unnatural bases, noncanonical bases, and modified bases. Polynucleotides also include oligonucleotides. Unless specifically described as excluding other types of polynucleotides, DNA may be interpreted as a general term that encompasses polynucleotides broadly. Synthetic polynucleotides are polynucleotides with non-natural sequences that are not derived from natural or biological sources. Polynucleotides may be single-stranded, double-stranded, or partially double-stranded (e.g., having a "sticky end").

The synthetic polynucleotides of this disclosure may be synthesized by any suitable technique for generating polynucleotides with specific sequences. Multiple techniques for generating synthetic polynucleotides are known to persons of ordinary skill in the art. Techniques for creating synthetic polynucleotides with specific sequences include the well-known nucleoside phosphoramidite method as well as enzymatic single-nucleotide addition using a template-independent polymerase. One example technique for enzymatic synthesis is described in Palluk, Sebastian, et al. "De novo DNA synthesis using polymerase-nucleotide conjugates." *Nature biotechnology* 36.7 (2018): 645-650.

The techniques of this disclosure involve hybridization of single-stranded polynucleotides. The sequence of polynucleotides or polynucleotide regions that hybridize with each other may be complementary, but it is understood that they need not be 100% complementary. As used herein, the terms "complementary" or "complementarity" are used in reference to polynucleotides related by the base-pairing rules. "Complementary" or "complementarity" refers to the nucleotides of a nucleic acid sequence that can bind to another nucleic acid sequence through hydrogen bonds, e.g., nucleotides that are capable of base pairing, e.g., by Watson-Crick base pairing or other base pairing. Nucleotides that can form base pairs, e.g., that are complementary to one another, are the pairs: cytosine and guanine, thymine and adenine, adenine and uracil, and guanine and uracil. Complementarity may be "partial," in which only some of the nucleic acids' bases are matched according to the base-pairing rules. Or there may be "complete" or "total" complementarity between the nucleic acids. The degree of complementarity between oligonucleotides has significant effects on the efficiency and strength of hybridization between nucleic acid strands.

Oligonucleotide sequences that hybridize to each other may have, at least 50%, at least 60%, at least 70%, at least 80%, at least 90%, at least 95%, at least 99%, or 100% sequence complementarity. Percent complementarity between particular stretches of oligonucleotide sequences can be determined routinely using software such as the BLAST programs (basic local alignment search tools) and PowerBLAST programs known in the art (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489).

As used herein, the term "hybridization" is used in reference to the pairing of complementary nucleic acids. Hybridization and the strength of hybridization (e.g., the strength of the association between the nucleic acids) is influenced by such factors as the degree of complementary between the nucleic acids and the stringency of the conditions involved. "Hybridization" methods involve the annealing of one nucleic acid to another, complementary nucleic acid, e.g., a nucleic acid having a complementary nucleotide sequence. The ability of two polynucleotides comprising complementary sequences to find each other and anneal through base pairing interaction is a well-recognized phenomenon. The initial observations of the "hybridization" process by Marmur and Lane, Proc. Natl. Acad. Sci. USA 46:453 (1960) and Doty et al., Proc. Natl. Acad. Sci. USA 46:461 (1960), have been followed by the refinement of this process into a well-understood tool of modern biology.

The techniques of this disclosure use toehold-mediated DNA strand displacement (DSD). DSD is an enzyme-free molecular tool to exchange one strand of a polynucleotide (output) with another strand (input). It is based on the hybridization of two complementary polynucleotide strands via Watson-Crick base pairing (A-T/U and C-G) and makes use of a process called branch migration. DSD starts with a double-stranded polynucleotide complex composed of the original strand and a protector strand. The original strand has an overhanging region the so-called "toehold" which is complementary to a third polynucleotide strand referred to as the "invading strand". The invading strand is a single-stranded polynucleotide (e.g., ssDNA) which is complementary to the original strand. The toehold regions initiate the process of DSD by allowing the complementary invading strand to hybridize with the original strand, creating a polynucleotide complex composed of three strands. After the binding of the invading strand and the original strand occurred, branch migration of the invading domain then allows the displacement of the initial hybridized strand (protector strand). DSD is well understood by persons of ordinary skill in the art and is described in Yurke, Bernard (2000). "A DNA-fueled molecular machine made of DNA". Nature. 406 (6796): 605-8 and David Yu Zhang and Georg Seelig. *Dynamic dna nanotechnology using strand displacement reactions*. Nature Chemistry, 3(2):103-113, 2011.

Detail of procedures and techniques not explicitly described or other processes disclosed of this application are understood to be performed using conventional molecular biology techniques and knowledge readily available to one of ordinary skill in the art. Specific procedures and techniques may be found in reference manuals such as, for example, Michael R. Green & Joseph Sambrook, *Molecular Cloning: A Laboratory Manual*, Cold Spring Harbor Laboratory Press, $4^{th}$ ed. (2012).

FIG. 1A shows the use of a polynucleotide taggant 100 to label and identify an item 102. Polynucleotide taggants 100 are powerful tags that can be easily applied to materials or object in any shapes and sizes. They are particularly useful for supply chain tracking and labeling high-value items. A polynucleotide taggant 100 contains multiple synthetic polynucleotides 104 that collectively encode a bit sequence using both the sequences of the individual synthetic polynucleotides and their hybridization states (i.e., single-stranded or double-stranded). The polynucleotide taggant 100 is designed in silico and the necessary polynucleotides are synthesized. There will typically be many copies of each of the individual synthetic polynucleotides 104 in the polynucleotide taggant 100. Some or all of the synthetic polynucleotides 104 are applied to the item 102.

The item 102 may be a high-value item such as a work of art, a jewel, a banknote, a document, an antique, etc. The synthetic polynucleotides 104 may be placed directly on the surface of the item 102 for example in liquid or powder form. If the item 102 itself is liquid, the synthetic polynucleotides 104 may be mixed into the item 102. The synthetic polynucleotides 104 may be applied "naked" without any modification or they may be protected with stabilizing agents or encapsulated by a protective coating. Multiple techniques for stably storing polynucleotides have been developed for storing biological samples and are known to those of ordinary skill in the art. Any suitable technique may be adapted for use with the item 102 depending on the structure of the item 102. In some implementations, the synthetic polynucleotides 104 may be placed on, under, or in a second taggant that is visibly detectable such as a QR code, RFID tag, or holographic sticker.

Because some of the information encoded by the synthetic polynucleotides 104 is encoded using hybridization states, the synthetic polynucleotides 104 are pre-hybridized as necessary to create the polynucleotide taggant 100. Once created, the polynucleotide taggant 100 is preferably kept below the melting temperature of the double-stranded polynucleotides so that the hybridization state is not lost or altered. The same polynucleotide taggant 100 may be applied to multiple different items 102 (e.g., added to multiple bottles of the same wine) or be unique to one particular item 102 (e.g., used only for one piece of artwork).

A sample of the polynucleotide taggant 100 may be collected from the item 102 by swabbing the surface, removing a portion of the item 102 and extracting the polynucleotides, rinsing the item 102 and extracting polynucleotides from the rinse solution, or by another technique. For example, techniques developed for environmental or forensic samples may be used to collect and process the synthetic polynucleotides 104 collected from the item 102.

See Hinlo R., Gleeson D., Lintermans M., Furlan E. (2017) *Methods to maximise recovery of environmental DNA from water samples*. PLoS ONE 12(6) and Butler, John M. *Forensic DNA Typing—Biology, Technology, and Genetics of STR Markers*" Second Edition, Elsevier Academic Press, Burlington, MA (2005).

If the item 102 is authentic, the polynucleotide taggant 100 will be present in the collected sample. However, if a counterfeit tag is applied to the item 102, polynucleotides collected in the sample will not be the same as the polynucleotide taggant 100.

The polynucleotides collected from the item 102 are applied to a substrate 106. The substrate 106 may also be referred to as a "ticket" and is generally formed from a flat fibrous material to which polynucleotides can be attached. In one implementation, the substrate 106 is a nitrocellulose membrane. Additionally or alternatively, the substrate may be an eggshell membrane (ESM), for example. It has been demonstrated that ESM treated with acetic acid or n-butyl acetate can be used to immobilize nucleic acids having terminal amine groups. Other materials, such as nylon membranes, nanofibers, and chitosan-modified membranes, for example, may be used as the substrate 106.

The substrate 106 has disposed upon its surface a plurality of physically separated assay locations 108. Collections of membrane bound polynucleotide complexes are attached to the substrate 106 at each assay location 108. Specific techniques for attaching the polynucleotide complexes to the substrate 106 will depend on the material from which the substrate 106 is made. The membrane bound polynucleotide complexes interact with the synthetic polynucleotides 104 and undergo some type of detectable change if hybridization occurs. All of the membrane bound polynucleotide complexes attached to a given assay location 108 can have the same sequences. The assay locations 108 may be arranged in a number of patterns on the surface of the substrate 106. FIG. 1 shows the assay locations 108 arranged in a grid pattern. However other arrangements are also possible such as a line, a circle, etc. The plurality of physically separated assay locations may include at least 4, 5, 6, 7, 8, 9, 10, 11, 12, 13, 14, 15, 16, 17, 18, 19, 20, 21, 22, 23, 24, 25, or more separate assay locations on each substrate.

During manufacturing of a substrate 106, the assay locations 108 may be formed, and thus a pattern created on the surface of the substrate 106, by depositing a pattern of hydrophobic barriers with a wax-based printer. When the wax is heated, it permeates the nitrocellulose membrane, thereby forming hydrophobic barriers to physically separate the assay locations 108 from one another. However, it will be understood that other techniques besides wax printing may be used to delineate separate assay locations 108 upon the surface of the substrate 106.

The substrate 106 is associated with a validation code 110. The validation code 110 may be any type of identifier such as a string of human-readable letters or numbers, a barcode, a quick-response (QR) code, or the like. The validation code 110 may be physically attached to the substrate 106 such as by printing or marking on the surface of the substrate 106. Alternatively, the validation code 110 may be associated with the substrate 106 without being physically attached to the substrate 106. For example, a package containing the substrate 106 may be marked with the validation code 110 or the package may contain another item such as a piece of paper that has the validation code 110.

Polynucleotides collected from the item 102 (the polynucleotide taggant 100 if the item 102 is authentic) are brought into contact with the substrate 106. This can be done, for example, by incubating the substrate 106 in a solution containing the collected polynucleotides. In one implementation, the substrate 106 is placed in a container (e.g., a petri dish) and a solution that contains polynucleotides collected from the item 102 is added so that it covers the surface of the substrate 106. Alternatively, a solution containing the polynucleotides collected from the item 102 may be added separately to each of the assay locations 108 such as with a dropper or pipette. The collected polynucleotides are allowed to incubate with the substrate 106 under conditions and for a duration sufficient for polynucleotide hybridization to occur. For example, incubation may be performed for 20 minutes at room temperature followed by allowing the substrate 106 to air dry.

Contacting the substrate 106 with the polynucleotides collected from the item 102 may result in a detectable change at one or more of the assay locations 108 that results in the appearance of a detectable pattern 112 on the substrate 106. The detectable pattern 112 is generated by hybridization of synthetic polynucleotides 104 in the polynucleotides taggant 100 with bound polynucleotide complexes on the substrate 106. The detectable pattern 112 may be created by any type of detectable change that can result from polynucleotide hybridization. For example, the detectable pattern 112 may be created by a change in fluorescence, a change in emitted light, a change in reactivity, a change in magnetism, etc.

On implementation of a DNA tagging system that allows DNA tags to be rapidly read on a paper ticket using fluorescence is described in Berk, Kimberly L., et al. "Rapid visual authentication based on DNA strand displacement." *ACS Applied Materials & Interfaces* 13.16 (2021): 19476-19486. With this technique a DNA taggant (barcode) can trigger a unique, sequence-driven pattern on a DNA-reporter paper. The techniques of Burke et al. may be adapted for use with the substrate 106 described in this disclosure. For example, a source of ultra-violet light such as an e-gel reader may be used to generate light at the excitation waveband for the fluorophores. A filter may be used so that the light emitted from the fluorophores can be observed by a user or captured with a conventional visual light camera.

Figure 1B:
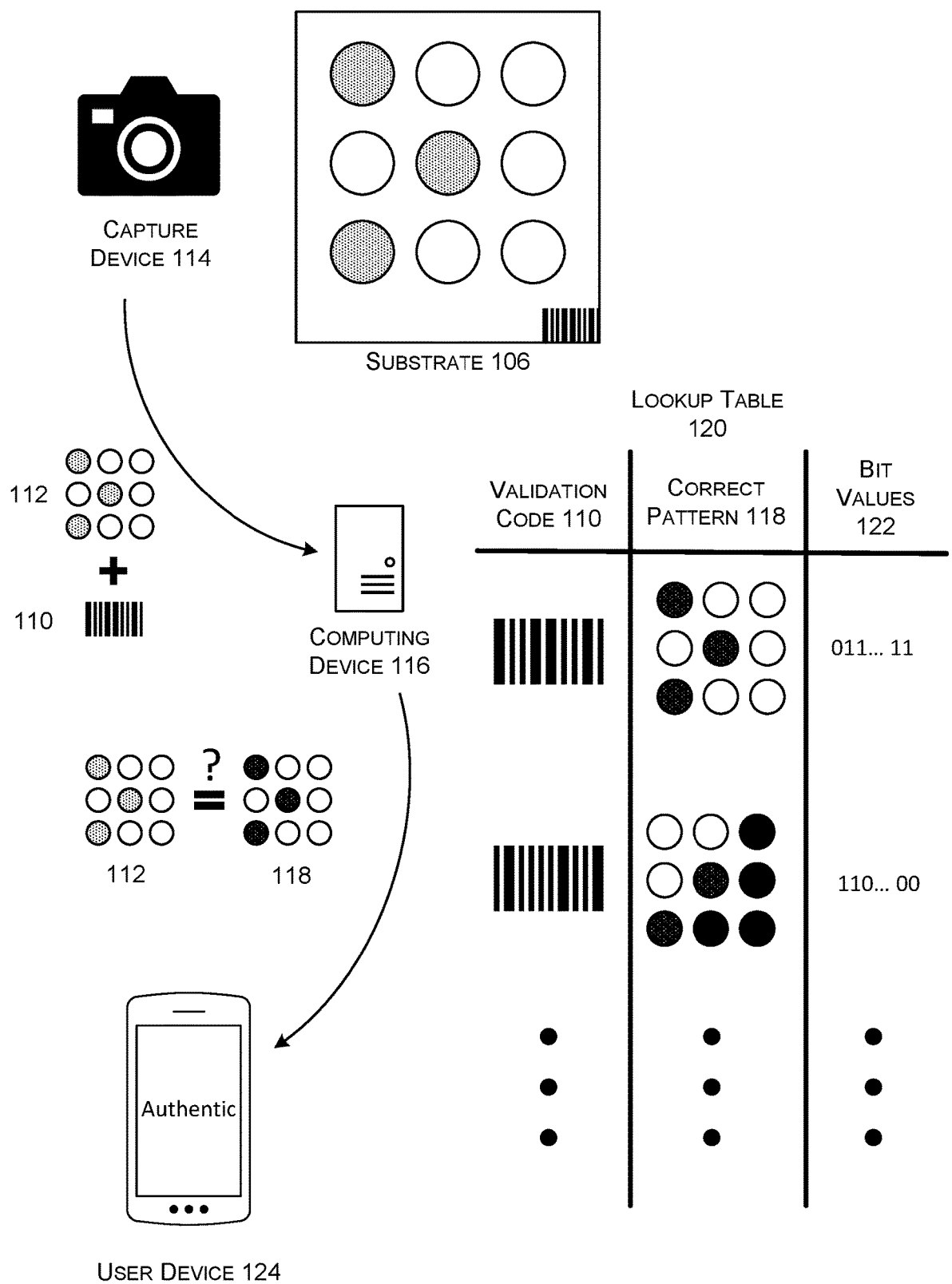

FIG. 1B illustrates capture on the detectable pattern 112 on the substrate 106 and evaluation of that pattern to determine if the item 102 (as evidenced by the polynucleotide taggant 100) is authentic or not. A capture device 114 captures the detectable pattern 112 and the validation code 110 from the substrate 106. If the detectable pattern 112 is created by a visible change in the substrate 106 then the capture device 114 may implement it as a camera. For example, the capture device 114 may be implemented as a mobile phone that includes a camera. If the detectable pattern 112 is created by a different type of signal, such as radioactivity or magnetism, a capture device 114 capable of detecting that type of signal will be used.

There may be an application installed on the capture device 114 specifically for interpreting an image or other signal captured from the substrate 106. For example, the capture device 114 may detect an orientation of the substrate 106 based on the shape of the substrate 106 and/or the presence of a fiducial. The validation code 110 may act as a fiducial if it is present on the substrate 106. Other types of fiducial such as a clipped corner of the substrate 106 may be used to detect the orientation. The capture device 114 may then use a computer vision pipeline to identify which assay locations 108 are emitting (or have ceased to emit) a signal.

This can be correlated with bit locations of the bits encoded by the polynucleotide taggant 100 to determine bit values 122.

The capture device 114 is configured to send the detectable pattern 112 and the validation code 110 to a computing device 116. Alternatively, the detectable pattern 112 may be interpreted by the capture device 114 as described above and only the bit values 122 are provided to the computing device 116. The computing device 116 is configured to receive the detectable pattern 112 and the validation code 110 captured by the capture device 114. The capture device 114 may communicate with the computing device 116 via a network such as the Internet. The computing device 114 may be any type of conventional computing device such as, but not limited to, a server, a network-accessible computing device, a cloud-based system, or the like. In some implementations, the computing device 116 may also be a local computing device that is accessible to a user of the capture device 114. The computing device 116 may be the capture device 114. However, to make the decoding process less vulnerable to attacks by a bad actor it may be preferable for the computing device 116 to be accessible via a network and not directly accessible to the user.

The computing device 116 uses the validation code 110 to identify a correct pattern 118 that should be observed on the substrate 106 if the polynucleotide taggant 100 is authentic. The validation code 110 provides the computing device 116 with information to identify the correct pattern for the substrate 106. The computing device 116 compares the detectable pattern 112 to the correct pattern 118 to determine if they are a match. The intensity of a signal at each assay location 108 may be converted to a binary value as part of performing the comparison. The signal taken at each assay location 108 may be measured as a change in signal strength before the substrate 106 was contacted with that polynucleotide taggant 100 and after. Thus, the polynucleotide taggant 100 may cause each assay location 108 to exhibit an increase or decrease in signal. The strength of a signal at a given assay location 108, including the amount of change in strength of the signal, may be converted from a measured value for a fluorescence level to an indication of either fluorescence or no fluorescence.

There are multiple possible ways that the computing device 116 may use the validation code 110 to identify the correct pattern 118. In one implementation, the computing device uses a lookup table 120 to correlate the validation code 110 with the correct pattern 118 for the substrate 106. The lookup table 120 may include entries for multiple different pairs of validation codes 110 and correct patterns 118. Each validation code 110 acts as an entry to query the lookup table 120. The lookup table 120 may also include bit values 122 encoded by the portion of the polynucleotide taggant 100 detected by the substrate 106. These bit values 122 themselves may be encoded by the validation code 110. Thus, in one implementation, lookup table 120 does not include the validation code 110 as such but first decodes it into a string of bits and then uses the bit values 122 to look up the correct pattern 118.

In another implementation, the validation code 110 may itself encode the correct pattern 118. For example, the validation code 110 (e.g., implemented as a QR code) may communicate to the computing device 116 which bits from the polynucleotide taggant 100 are read by the substrate 106 and the locations where individual ones of those bits are detected on the substrate 106. With this information, the computing device 116 can be programmed to determine if the detectable pattern 112 matches a correct pattern 118. The validation code 110 may also be encrypted with a secret key to prevent a bad actor from identifying which bits are read out by the substrate 106. For example, the validation code 110 may include a hash value that is decoded using a key kept by the computing device 116.

In one implementation, the validation code 110 is unique to each substrate 106. That is, each individual ticket or piece of material that functions as a substrate 106 is associated with a different validation code 110. The computing device 116 may be configured to recognize multiple attempts to submit the same validation code 110 and return an error or "inauthentic" message if the same validation code 110 is submitted more than a threshold number of times. For example, the computing device 116 could enforce a single use rule for each validation code 110. This will thwart attacks in which a bad actor attempts to copy a valid substrate 106 to make fake substrates that always generate a correct pattern. Even if a fake substrate generates the correct pattern 118—it will not receive a successful validation message from the computing device 116 if the validation code 110 was already used.

If the computing device 116 determines that there is a match between the detectable pattern and the correct pattern 118, then an indication of authenticity (or inauthenticity) can be sent from the computing device 116 to a user device 124. The user device 124 may render the determination in any manner that can be output to the user. For example, the user device 124 may display an indication on a screen or generate an audible tone. The user device 124 may be implemented as a hand-held device such as a mobile phone. In some implementations, the user device 124 is the same as the capture device 114.

Figure 2A:
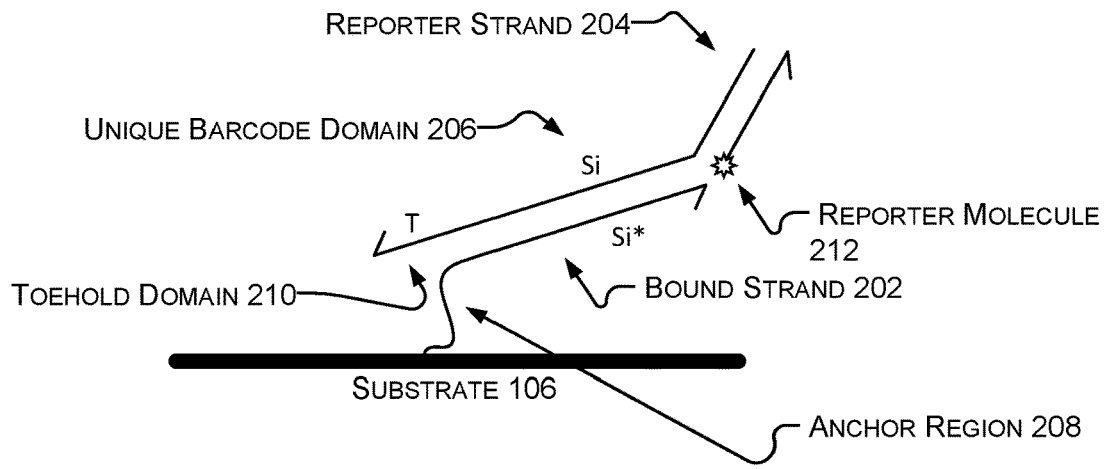
FIG. 2A illustrates a bound polynucleotide complex.

FIG. 2A illustrates the structure of a bound polynucleotide complex 200. The bound polynucleotide complexes 200 are attached to the substrate 106 at the assay locations 108. The specific sequences of the bound polynucleotide complexes 200 are different at each assay location 108. The bound polynucleotide complexes 200 are configured to detect bit values of the polynucleotide taggant 100 by hybridization to the synthetic polynucleotides 104 in the polynucleotide taggant 100. The hybridization may lead to participation in DSD reactions that result in displacement of strands of the bound polynucleotide complexes 200. DSD is a competitive hybridization reaction whereby an input DNA strand displaces a previously "bound" output strand from a complementary binding partner. DSD techniques are well known to those of ordinary skill in the art and described in Each bound polynucleotide complex 200 includes a bound strand 202 and a reporter strand 204 that are hybridized to each other. The portions of the two strands that are hybridized to each other include a unique barcode domain (Si/Si*) 206 and may also include a universal domain (not shown). The unique barcode domain 206 indicates a bit position in a bit sequence encoded by the polynucleotide taggant 100. Thus, it is the unique barcode domain 206 that determines which bit from a polynucleotide taggant 100 is detected by a given assay location 108 on the substrate 106. The universal domain, if present, may be an either or both sides of the unique barcode domain 206 and is common to all bound polynucleotide complexes 200 across all of the assay locations 108.

The bound strand 202 is attached to the substrate 106 by an anchor region 208. The anchor region 208 may be designed to be a poly-thymine ((poly)T) tail at either the 3'- or the 5'-end of the bound strand 202 that binds to a nitrocellulose membrane. However, multiple other techniques may be used to attach the bound strand 202 to the substrate 106. For example, an end of the bound strand 202 may be modified with biotin such that it can form a strong bond with a streptavidin-coated membrane.

The reporter strand 204 includes a toehold domain (T) 210. However, in other implementations the toehold domain 210 may be present on the bound strand 202. The toehold domain 210 is a short region that is used to initiate the strand displacement reaction. The toehold domain 210 may comprise eight or fewer nucleotides.

The reporter strand 204 includes a reporter molecule 212. FIG. 2A illustrates the reporter molecule 212 as attached to a third polynucleotide strand that is hybridized to the reporter strand 204. However, the reporter molecule 212 may be attached to the bound polynucleotide complex 200 in many different ways. For example, the reporter molecule 212 may be attached directly to the reporter strand 204. It is also possible, in some configurations, for the reporter molecule 212 to be attached to the bound strand 202. In such configurations, the reporter strand 204 may include a quencher that prevents detection of the reporter molecule 212 when the reporter strand 204 is hybridized to the bound strand 202.

The reporter molecule 212 may be implemented as any type of molecule or tag that can generate a detectable signal. For example, the reporter molecule 212 may be implemented as any one of a number of types of fluorophores that are commonly used for visualizing polynucleotides. The reporter molecule 212 may also be implemented as a dye or other type of molecule that is visually detectable without fluorescence. The reporter molecule 212 may be a metal or other magnetized material that can be detected by the presence of a magnetic field. The reporter molecule to 212 could alternatively be implemented as a radioactive molecule that can be detected by the presence of radiation.

The bound polynucleotide complex 200 generates a detectable signal due to the separation of the reporter strand 204 from the bound strand 202. The separation is caused by an invading strand hybridizing to the toehold domain 210 and displacing the reporter strand 204. As mentioned above, the toehold domain 210 may be on either of the reporter strand 204 or the bound strand 202. Once disassociated, washing of the substrate 106 removes the reporter strand 204 and may also remove the reporter molecule 212 if it is attached to the reporter strand 204. This may be detected as a decrease in signal due to the loss of the report of molecule 212.

Figure 2B:
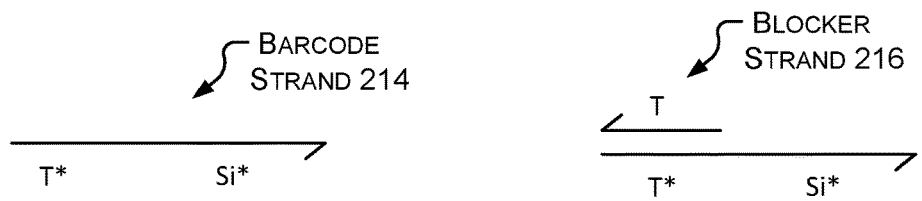
FIG. 2B illustrates synthetic polynucleotides that are included in a polynucleotide taggant.

FIG. 2B illustrates synthetic polynucleotides 104 that can encode a bit value from a polynucleotide taggant 100. This polynucleotide encoding scheme encodes a bit sequence, which could be a barcode, in the hybridization state of polynucleotides. For example, 1s are represented by single-stranded polynucleotides—barcode strand 214, and 0s are represented by partially double-stranded polynucleotides—barcode strand 214 hybridized to a blocker strand 216. However, the convention could be reversed so that 0s are represented by the single-stranded molecules while 1s are represented by the partially double-strand molecules. Because the information is encoded in the hybridization states of the polynucleotides, simply sequencing a captured polynucleotide taggant 100 cannot reveal the bit sequence encoded by the polynucleotide taggant 100.

The barcode strand 214 includes a first domain (T*) that hybridizes to the toehold domain 210. Thus, the barcode strand 214 will function as an invading strand in a DSD reaction with the bound polynucleotide complex 200. Each barcode strand 214 also includes a second domain (Si*) that hybridizes to the unique barcode domain 206. It will hybridize to either the reporter strand 204 or the bound strand 202 dependent which strand has the toehold domain 210. The barcode strand 214 may also include a universal domain (not shown) that hybridizes to the universal domain. The process starts when the barcode strand 214 (e.g., T* Si*) hybridizes to the reporter strand 204 at the uncovered toehold domain (T) 210 and then undergoes branch migration through the universal domain, if present, and the barcode domain (Si). At the end of the reaction, the previously bound reporter strand 204 labeled with reporter molecule 212 will fall off the bound polynucleotide complex 200. The barcode strand 214 may be at least 15 nucleotides long, such as 20 nucleotides to 30 nucleotides long.

In DSD reactions, polynucleotide strands should interact only with their complementary strands. However, they can hybridize even if sequences are partially complementary. Thus, the polynucleotide taggant 100 and the substrate 106 are designed so that the barcode strand 214 only functions as an invading strand for the bound polynucleotides complexes 200 which have the same unique barcode domain (Si) 206. This prevents crosstalk between synthetic polynucleotides 104 which are intended to represent different bits in the bit sequence encoded by the polynucleotide taggant 100. Thus, all of the unique barcode domains 206 used in a given polynucleotide taggant 100 are designed in silico to have high sequence orthogonality which will prevent such crosstalk. The specificity of the unique barcode domain 206 means that each barcode strand 214 will only stably hybridize to an assay location 108 intended to detect that specific bit.

The polynucleotide taggant 100 encodes multiple bits that each is 0 or 1 and are each represented by either the barcode strand 214 as a single-stranded molecule or hybridized to a blocker strand 216. Thus, in a given polynucleotide taggant 100, all the synthetic polynucleotides 104 that can hybridize to a unique barcode domain 206 (Si) are either single-stranded or they are all either hybridized to a blocker strand 216. The blocker strand 216 is at least the length of the toehold domain 210 but may be longer including up to the full length of the barcode strand 214. If present, the blocker strand 216 prevents the barcode strand 214 from acting as an invading strand and prevents the DSD reaction.

In an implementation that is not shown, the synthetic polynucleotides 104 include the reporter molecules 212 so that hybridization results attachment of the reporter molecules to attend to the substrate 106. In this implementation, the bound polynucleotide complex 200 would not include the reporter molecule 212. A successful DSD reaction would then result in an increase in the signal.

In another implementation, the barcode strand 214 includes a quencher molecule. The quencher molecule, when hybridized to the bound strand 202 can suppress the activity of a reporter molecule 212 attached to the bound strand 202. Thus, there are multiple possible configurations that could be implemented to result in a change in signal, either increase or decrease, that results from hybridization of the barcode strand 214 to one of the strands of a bound polynucleotide complex 200. All variations described above as well as others that could be readily appreciated by one skilled in the art are understood to be potential implementations of the bound polynucleotides complexes 200 and the synthetic polynucleotides 104.

Figure 3:
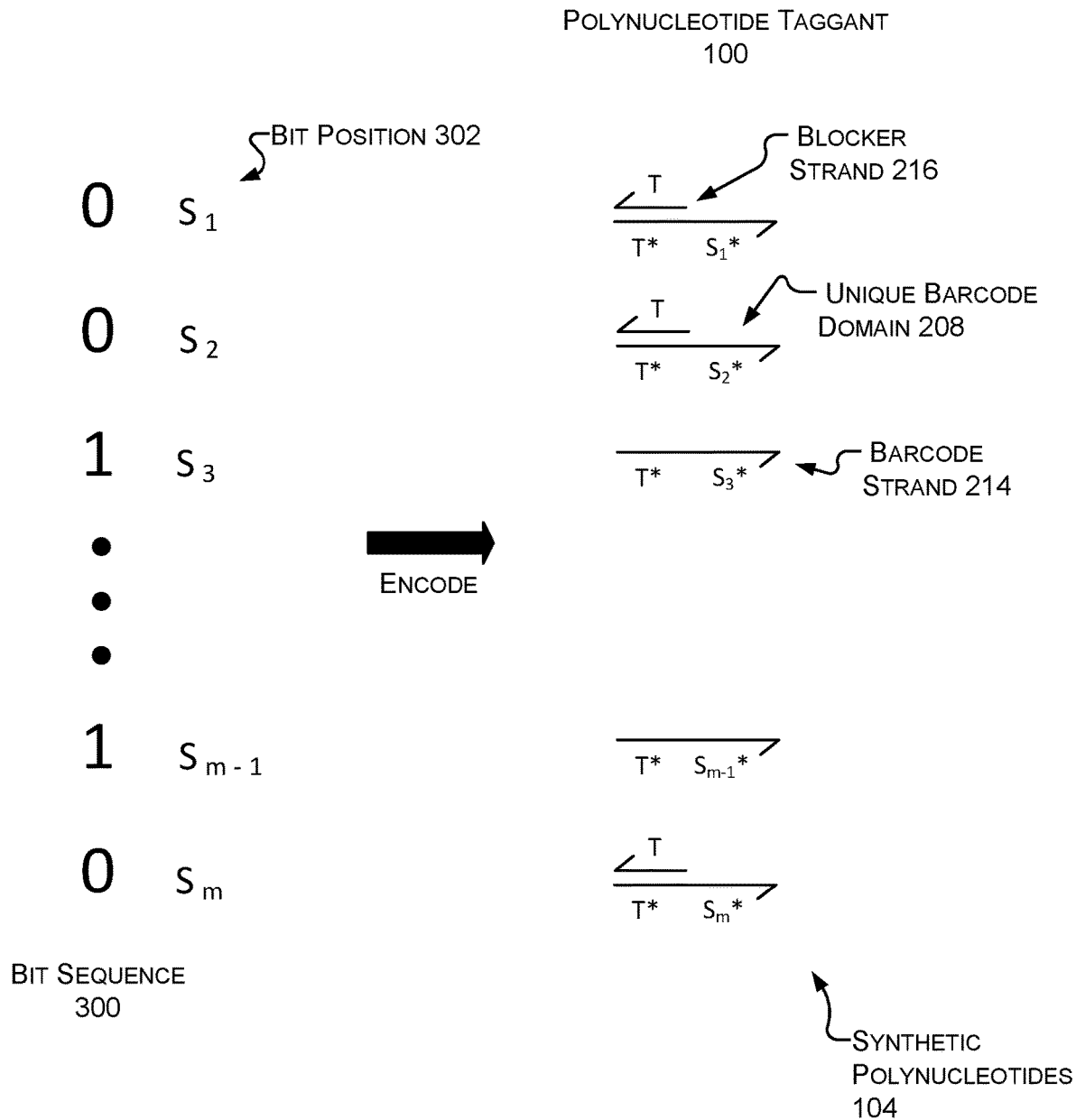
FIG. 3 illustrates how the sequences of unique barcode domains encode bit positions of a bit sequence encoded by a polynucleotide taggant.

FIG. 3 illustrates how a set of synthetic polynucleotides 104 that make up a polynucleotide taggant 100 can encode a bit sequence 300. A bit sequence 300 is a series of bits in a specific order such that each bit in the bit sequence 300 occupies a specific bit position 302. A polynucleotide taggant 100 may encoded bit sequence 300 of any length such as from 3 to 1000 bits and may typically be about 25 to 100 bits. Because the polynucleotide taggant 100 is not a single polynucleotide but rather a collection of multiple separate synthetic polynucleotides 104, the bit position 302 must be encoded in each of the synthetic polynucleotides 104. The bit position 302 is encoded by the unique barcode domain 206 (Si). In the example shown FIG. 3, the bit sequence 300 includes m bit positions 302. Each is represented by $S_1$, $S_2$, $S_3$, ..., $S_{m-1}$, and $S_m$.

The polynucleotide taggant 100 encodes, for each bit in the bit sequence 300, either a first bit value (e.g., 1) by a single-stranded synthetic polynucleotide or a second bit value (e.g., 0) by the single-stranded synthetic polynucleotide hybridized to a blocker strand. Thus, for each bit position 302 in the bit sequence 300 there will be a synthetic polynucleotide 104 is either a single-stranded molecule or that is hybridized to a blocker strand.

The synthetic polynucleotides 104 that are hybridized to a blocker strand 216 (e.g., representing 0 bits) do not perform DSD reactions with or hybridized to the bound polynucleotide complexes 200 attached to the substrate 106. However, if they are not included in the polynucleotide taggant 100 it could be vulnerable to sequencing attacks. Without the partially double-stranded polynucleotides, the only polynucleotides in the polynucleotide taggant 100 would be the single-stranded barcode strands 214. Those strands could be sequenced and reproduced creating a copy of the polynucleotide taggant 100. Thus, in order to prevent these types of attacks, the synthetic polynucleotides 104 that are hybridized to a blocker strand 216 are included in the polynucleotide taggant 100 even though they do not hybridize to the substrate 106.

The bit sequence 300 may be arbitrarily created to use as a tag for any type of item 102. Once the bit sequence 300 is selected, all the barcode strands 214 and blocker strands 216 necessary to encode that bit sequence 300 are separately synthesized. They are then pre-hybridized creating the partially double-stranded synthetic polynucleotides 104 used to encode one of the bit values (e.g., the 0s). Any excess blocker strands 216 are removed and all the synthetic polynucleotides 104 are combined to make the polynucleotide taggant 100.

In some implementations, the bit sequence 300 is simply a random series of bits. However, it may also be used to encode information as any can be done with any series of bits. For example, the bit sequence 300 may represent a hash or digital signature. It might also encode something linked to the physical item 102 such as a human-readable description of the item 102. For example, the bit sequence 300 could encode their word "red" and be used to tag a red wine. If the tag was found on a white wine, it would indicate that the polynucleotide taggant 100 and/or the item 102 is not authentic. Thus, information encoded in the bit sequence 300 can function as an additional layer of security.

Although this type of polynucleotide taggant 100 is resistant to sequencing attacks because hybridization states are used to encode information, the substrate 106 can be used to separate 1s from 0s. Thus, if a bad actor combines the substrate 106 with sequencing, it is possible to hack the polynucleotide taggant 100, resulting in a security loophole. This problem is present for implementations in which the substrate 106 can read "all" of the bit positions 302 in the bit sequence 300. This loophole is addressed as described in greater detail below by using substrates 106 that each individually read only a subset of the bits encoded by the polynucleotide taggant 100. For example, the polynucleotide taggant 100 may encode a bit sequence 300 with 100 bits and a substrate 106 reads only 25 of the bit positions 302. Thus, there are 75 of the 100 bits from the bit sequence 300 that cannot be discovered using the substrate 106.

Even if a bad actor identified the portion of the polynucleotide taggant 100 that was detected by a substrate 106, the other bits values 302—particularly the hybridization states—would remain unknown. The bad actor could attempt to make a fake tag, but it would be accurate only for those 25 bits detected by the substrate 106 used by the attacker. A different substrate 106 that detects a different set of bits from the bit sequence 300 would be able to identify the fake tag as counterfeit. Using a polynucleotide taggant 100 that encodes more bits than is detected by any single substrate 106 makes the polynucleotide taggant 100 asymmetrically difficult to hack.

Figure 4:
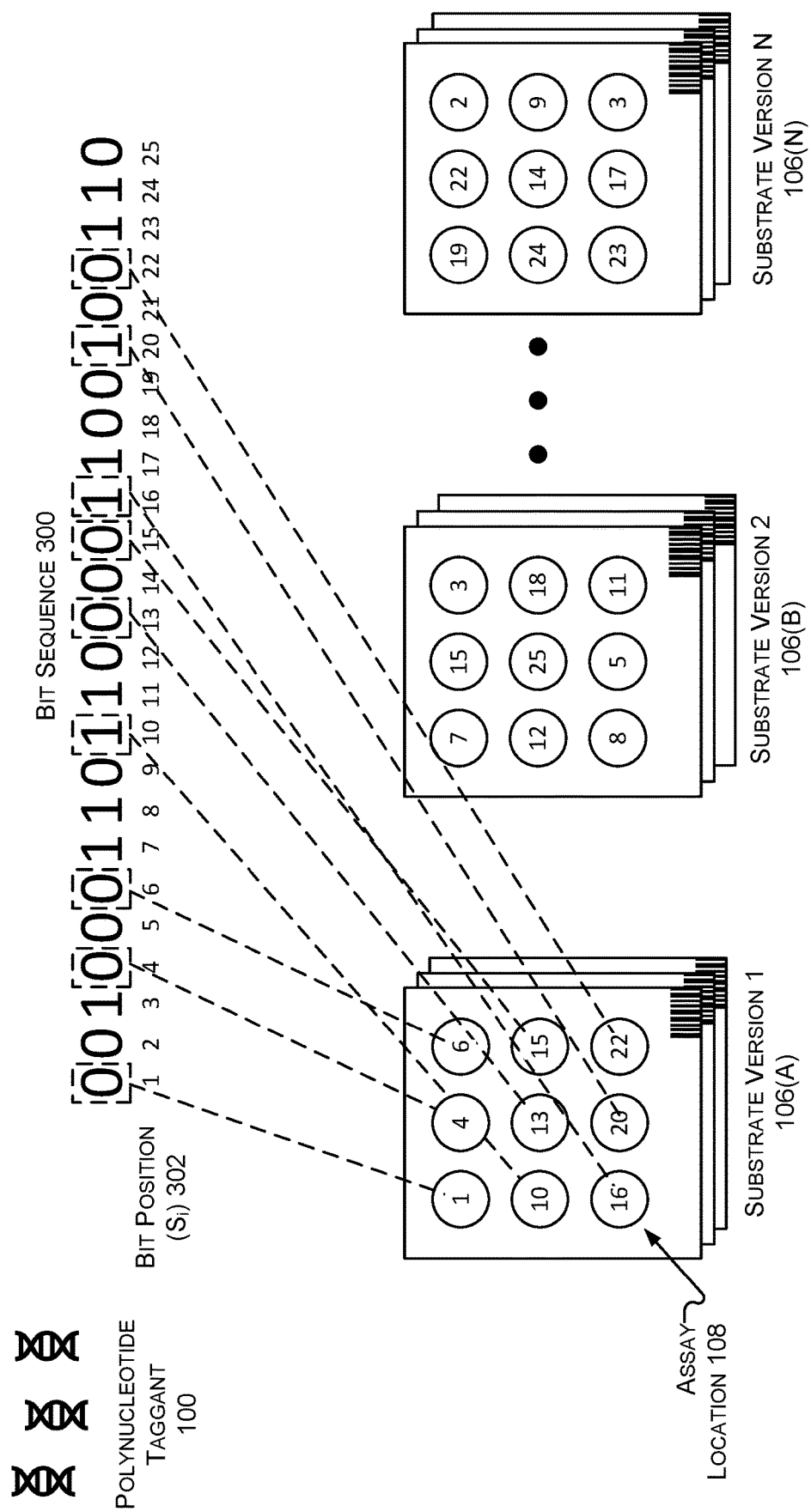
FIG. 4 illustrates multiple versions of a substrate that each detects different bits from a bit sequence.

FIG. 4 illustrates a plurality of different versions of the substrate 106(A), 106(B), ..., 106(N) that each recognize different bits from the bit sequence 300 encoded by the polynucleotide taggant 100. Any version of the substrate 106(A), 106(B), ..., 106(N) may be used to validate an item 102 tagged with the polynucleotides taggant 100. Thus, a system for authenticating an item 102 can include a plurality of substrates 106 each comprising a plurality of bound polynucleotide complexes 200 attached to the substrate 106. Individual users, or potential users, may receive only one or a few versions of the substrate 106. There can also be versions of the substrate 106 that are possible but not physically created. This would make it impossible for a bad actor to obtain a copy of these "latent" versions of the substrate 106. If a hack is suspected, new versions of the substrate 106 could be generated and distributed.

The bound polynucleotide complexes 200 on each substrate 106(A), 106(B), ..., 106(N) are configured to detect a different subset of the bits from the bit sequence 300 encoded by the polynucleotide taggant 100. This is shown by different numbers for the bit positions 302 at the assay locations 108 on each version of the substrate 106(A), 106(B), ..., 106(N). These numbers correspond to the Si bit positions 302 shown in FIG. 3 and to the unique barcode domain 206 shown in FIG. 2.

As described above, the bits in the bit sequence 300 are detected by hybridization of the bound polynucleotide complexes 200 to the synthetic polynucleotides 104 and generation of a detectable pattern on substrate 106. Because different versions of the substrate 106(A), 106(B), ..., 106(N) detect different bits each will likely, but not necessarily, generate different detectable patterns.

Each separate version of the substrate 106(A), 106(B), ..., 106(N) is associated with a different validation code. If there are multiple copies of a single version of the substrate 106(A) then each copy will have the same validation code. Alternatively, each of the plurality substrates may be associated with unique validation code 110. That is, the validation code 110 associated with any given substrate 106(A), 106(B), ..., 106(N) is found only on that substrate 106 and not any of the other substrate 106 that may be used to detect the polynucleotide taggant 100. The validation code 110 combined with the detectable pattern 112 is used by the computing device 116 to validate the polynucleotide taggant 100.

Figure 5:
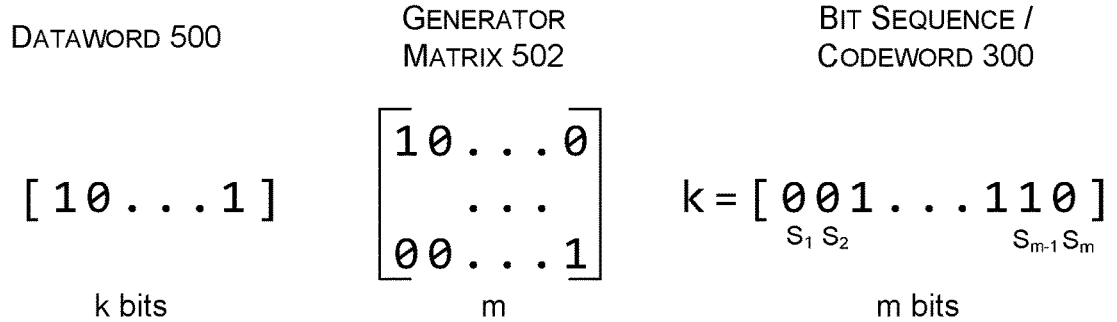
FIG. 5 illustrates how a subset of bits from a codeword can be used to recover a dataword.
Figure 5:
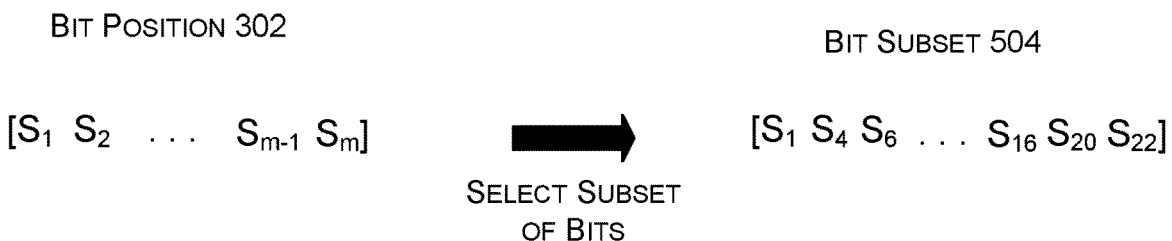

FIG. 5 illustrates an error correction and encoding scheme that enables recovery of a dataword 500 from the subset of bits in the bit sequence 300 detected by a single substrate 106. The bit sequence 300, which can also be referred to as a codeword, encoded by the polynucleotide taggant 100 may be used to encode arbitrary information such as information about the item 102. This information could be the name of the item 102, a characteristic of the item 102, the date the item was produced 102, or any other type of information. As mentioned above, the bit sequence 300 could decode to the word "red" for polynucleotide taggant 100 that is used to label a red wine.

However, because each individual substrate 100 only reads out a subset of the bits from the bit sequence 300, it is not be possible to reconstruct the entire bit sequence 300 from a random subset. The user would need to have a collection of substrates 106 that in aggregate could read out all of the bits from the bit sequence 300. Yet, if it is possible for a user to do this it would also be possible for a bad actor to use the substrates 106 in aggregate to reverse engineer and identify the hybridization states of the polynucleotide taggant 100. To address this, an encoding scheme is used to select the subset of bits from the bit sequence 300 in such a way that the bit sequence 300 can be recovered without identifying the hybridizing state of all of the synthetic nucleotides 104 in the polynucleotide taggant 100.

The dataword 500 of k bits is encoded into a bit sequence/codeword 300 of m bits, where m>k. The dataword 500 may be a binary vector that can be decoded to ASCII text or some other human-readable form. There are many different ways known to those of skill in the art for converting a dataword 500 into a codeword or bit sequence 300. One technique is by the use of a linear code. A linear code is an error-correcting code for which any linear combination of codewords is also a codeword. A generator matrix 502 can be used to generate the codewords of the code. The generator matrix 502 is a k×m matrix (where m is the length of the codewords) whose rows span the linear code of dimension k. By multiplying any k-dimensional dataword 500 by the generator matrix 502, one can generate a codeword. The generator matrix 502 can create $2^k$ code words. For example, each codeword is a row in the generator matrix 502 can be a codeword but there are other codewords that can be generated by the generator matrix 502.

The specific technique used for generating a codeword from a dataword 500 may also provide error correction. Error correction increases robustness of the decoding from the detected bits to the dataword 500. There may be errors introduced in the read out from a valid polynucleotide tag 100 due to degradation of the polynucleotides, ambiguous signals from the substrate 106, or other sources. Yet even with these types of errors, the dataword 500 can be recovered from a binary vector that is slightly different from the true bit sequence 300.

Selection of a bit subset 504 from the bit sequence 300 can be done by either relying on some particular known properties of the encoding scheme, or by selecting the subset arbitrarily and then verifying that it has the desired property with respect to the encoding scheme. The bit subset 504 is the subset of bits from the bit sequence 300 that are detected by a substrate 106 such as the selection of bit positions 302 shown in FIG. 4 as being mapped to a version of the substrate 106(A). Thus, this selection is done in advance of making a substrate 106. The bit subset 504 indicates which indices from the codeword 300 will be read by a substrate 106. This set of bits is sufficient to uniquely identify a single codeword 300 out of all possible codewords. Because there is a one-to-one mapping of codewords 300 to datawords 500 (given an encoding scheme) it is possible to recover the dataword 500 even though the bit subset 504 is less than the full bit sequence 300. The encoding scheme may be an encoding scheme such as linear code. In the case of a linear code, the bit subset 504 has the property that the linear code specified by the generator matrix 502 still has good Hamming distance even after a restriction to the coordinates in the bit subset 504. This allows identification of individual codewords 300 from only their coordinate values in the bit subset 504 even in the presence of errors. A brute force approach simply identifies random bit subsets 504 and then evaluates each to determine if a suitable codeword 300 can found using just the bits in the bit subset 504.

Illustrative Method

Figure 6:
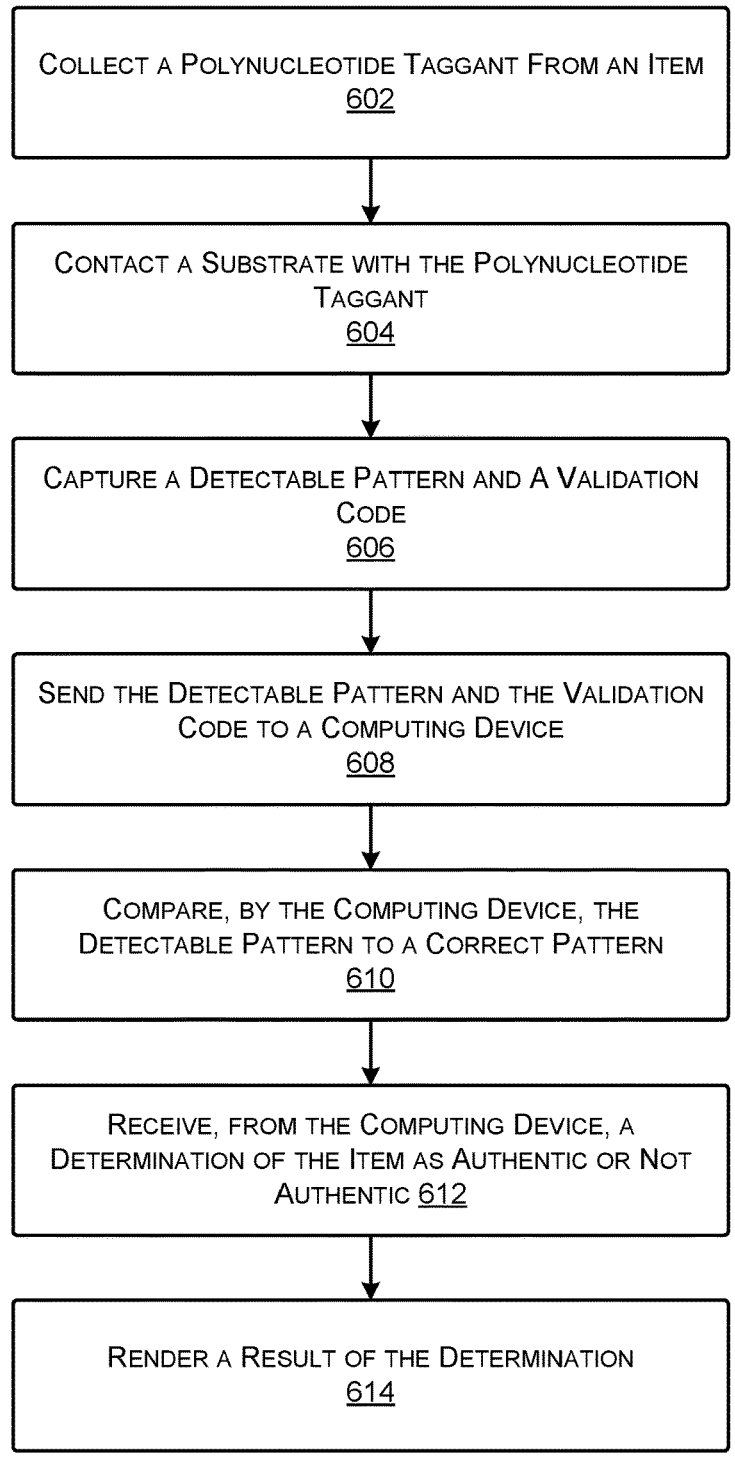
FIG. 6 is a flow diagram showing an illustrative method for using a polynucleotide tag to determine if an item is authentic.

FIG. 6 shows an illustrative process 600 for validating authenticity of an item by using a polynucleotide taggant that encodes a bit sequence in using the sequence and hybridization state of a plurality of synthetic polynucleotides.

At operation 602, a polynucleotide taggant is collected from an item. The polynucleotide taggant comprises a plurality of synthetic polynucleotides that collectively encode a bit sequence using the sequences of the polynucleotides and hybridization states of the polynucleotides. The synthetic polynucleotides encode, for each bit in the bit sequence, either a first bit value (e.g., 1) by a single-stranded synthetic polynucleotide or a second bit value (e.g., 0) by the single-stranded synthetic polynucleotide hybridized to a blocker strand.

The synthetic polynucleotides may be collected using any established techniques for collecting polynucleotides from environmental or forensic samples. Following collection, the synthetic polynucleotides may be cleaned or processed using commercial kits or any one of a number of techniques known to those of ordinary skill in the art.

At operation 604, a substrate is contacted with the polynucleotide taggant. For example, a solution containing the polynucleotide taggant may be applied to the surface of the substrate. The contact is performed under conditions suitable for polynucleotide hybridization. That is, conditions such as temperature, pH, and salt concentrations are suitable for hybridization including hybridization as part of a DSD reaction. Bound polynucleotide complexes on the substrate hybridize with the synthetic polynucleotides of the polynucleotide taggant. The hybridization results in emission of a detectable pattern from the substrate based on the bit values of the synthetic polynucleotides. The detectable pattern may be, for example, an increase or decrease of fluorescence at specific locations on the surface of the substrate. The substrate detects only a subset of bits in the bit sequence encoded by the polynucleotide taggant.

The substrate is one of a plurality of substrates that each validate the polynucleotide taggant and each detect a different subset of the bits in the bit sequence encoded by the polynucleotide taggant. In one implementation, the bound polynucleotide complexes detect bit values of the polynucleotide taggant by hybridization to the synthetic polynucleotides and participation in DSD reactions that result in displacement of strands of the bound polynucleotide complexes. This displacement results in the change in the detectable pattern. The detectable pattern may be a change in a signal resulting from displacement of reporter molecules bound to the substrate or attachment of reporter molecules to the substrate.

At operation 606, a detectible pattern and validation code are captured. The detectable pattern and the validation code are captured by capture device which may be a camera. The capture device detects and captures the detectable pattern. The validation code is a mark such as a barcode or a QR code. The validation code is associated with the substrate and may be a marking is physically present on the substrate. The validation code indicates a correct pattern for that substrate. The validation code may be unique to a single substrate or there may be multiple different substrates that share the same validation code. Detection of the correct pattern is used to validate that the polynucleotide taggant is authentic and thus any item tagged with the polynucleotide taggant is also authentic.

At operation 608, the detectable pattern and the validation code are sent to a computing device. The detectable pattern in the validation code are sent by the capture device to the computing device. For example, the capture device may send an image file via a communications network such as the Internet to the computing device.

At operation 610, the detectable pattern is compared to a correct pattern by the computing device. The computing device determines a correct pattern based on the validation code and performs a comparison of the detectable pattern to the correct pattern. The validation code may be used to look up the correct pattern in a lookup table. If the detectable pattern is the same pattern as the correct pattern then the computing device may determine that the polynucleotide taggant is authentic. The item may be determined to be authentic if the detectable pattern matches the correct pattern. In some implementations, a match is not limited to exact matches.

At operation 612, a determination of the item as authentic or not authentic is received from the computing device. The computing device that determines if there is a match may generate an indication of authenticity and send that indication to a different computing device such as a user device. The indication of authenticity may be an email or other electronic communication. In some implementations, the indication of authenticity may be encrypted. If, however, there is no match between the detected pattern and the correct pattern then the item may be determined to be inauthentic. A result of "not authentic" can be generated and sent by the computing device.

At operation 614, the results of the determination are rendered. The results may be rendered on the user device. Alternatively, if the computing device that performs the comparison is accessible to the user, the results may be rendered on the computing device. Rendering the results includes generating an output that is perceivable by the user such as a visual display on a screen or an audible tone. The user device may be a mobile phone or similar type of handheld communications device. The user device displays an indication of authenticity or an indication that the item could not be validated as authentic. The user device may be a computing device that is under the control of a purchaser or potential purchaser of the item. The results of the determination may be an error such as if a single use validation code was submitted more than once.

Illustrative Computer Architecture

Figure 7:
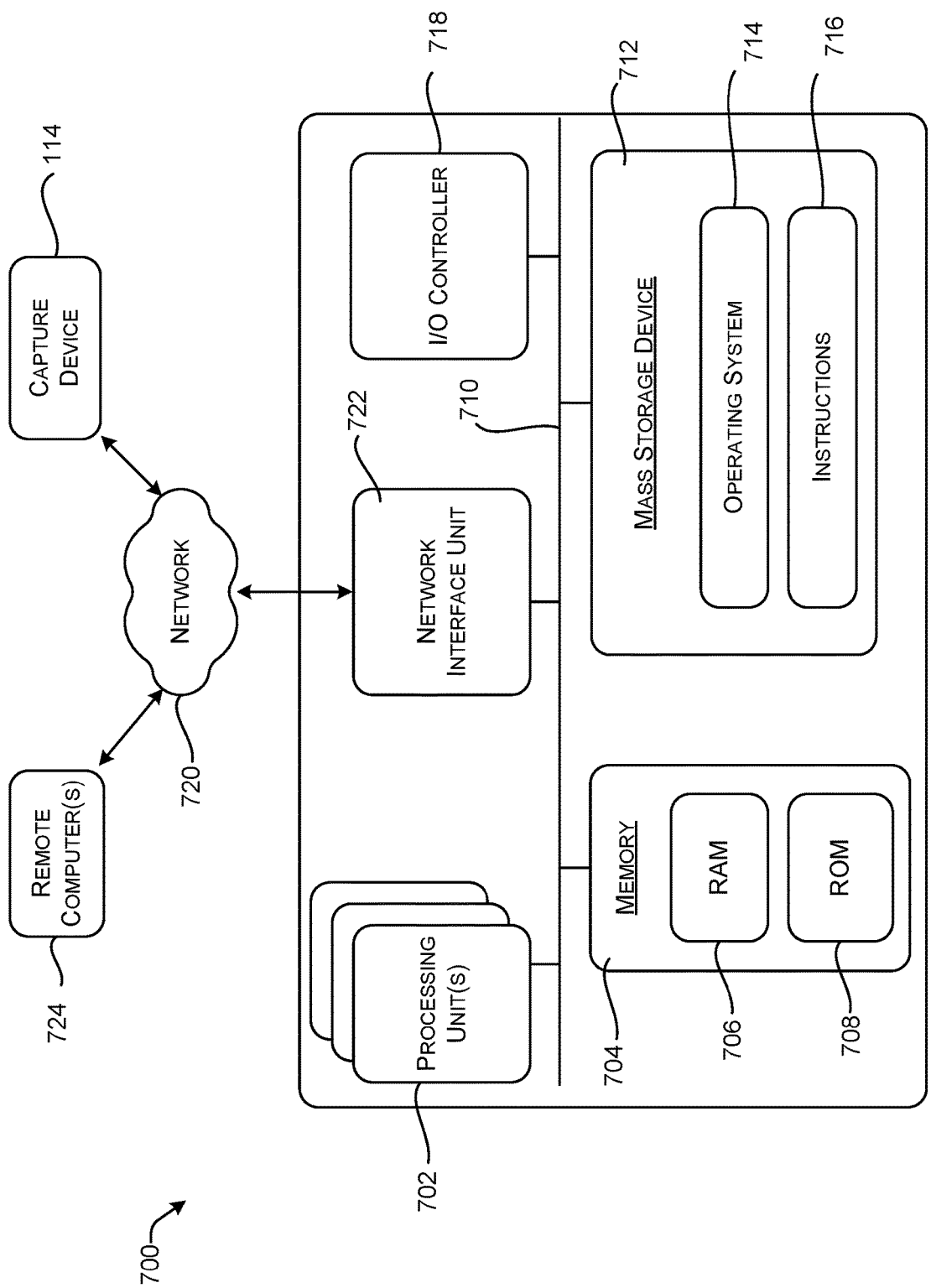
FIG. 7 is an illustrative computer architecture for implementing techniques of this disclosure.

FIG. 7 is a computer architecture diagram showing an illustrative computer hardware and software architecture for a computing device such as the computing device 116 or the user device 124 introduced FIG. 1. In particular, the computer 700 illustrated in FIG. 7 can be utilized to receive a detected pattern 112 and validation code 110 and/or to maintain a lookup table 120 as shown in FIG. 1.

The computer 700 includes one or more processing units 702, a system memory 704, including a random-access memory 706 ("RAM") and a read-only memory ("ROM") 708, and a system bus 710 that couples the memory 704 to the processing unit(s) 702. A basic input/output system ("BIOS" or "firmware") containing the basic routines that help to transfer information between elements within the computer 700, such as during startup, can be stored in the ROM 708. The computer 700 further includes a mass storage device 712 for storing an operating system 714 and other instructions 716 that represent application programs and/or other types of programs. The mass storage device 712 can also be configured to store files, documents, and data. In some implementations, lookup table 120 may be maintained in the mass storage device 712.

The mass storage device 712 is connected to the processing unit(s) 702 through a mass storage controller (not shown) connected to the bus 710. The mass storage device 712 and its associated computer-readable media provide non-volatile storage for the computer 700. Although the description of computer-readable media contained herein refers to a mass storage device, such as a hard disk, CD-ROM drive, DVD-ROM drive, or USB storage key, it should be appreciated by those skilled in the art that computer-readable media can be any available computer-readable storage media or communication media that can be accessed by the computer 700.

Communication media includes computer-readable instructions, data structures, program modules, or other data in a modulated data signal such as a carrier wave or other transport mechanism and includes any delivery media. The term "modulated data signal" means a signal that has one or more of its characteristics changed or set in a manner so as to encode information in the signal. By way of example, and not limitation, communication media includes wired media such as a wired network or direct-wired connection, and wireless media such as acoustic, radio frequency, infrared, and other wireless media. Combinations of any of the above should also be included within the scope of computer-readable media.

By way of example, and not limitation, computer-readable storage media can include volatile and non-volatile, removable and non-removable media implemented in any method or technology for storage of information such as computer-readable instructions, data structures, program modules, or other data. For example, computer-readable storage media includes, but is not limited to, RAM 706, ROM 708, EPROM, EEPROM, flash memory or other solid-state memory technology, CD-ROM, digital versatile disks ("DVD"), HD-DVD, BLU-RAY, 4K Ultra BLU-RAY, or other optical storage, magnetic cassettes, magnetic tape, magnetic disk storage or other magnetic storage devices, or any other medium that can be used to store the desired information and which can be accessed by the computer 700. For purposes of the claims, the phrase "computer-readable storage medium," and variations thereof, does not include waves or signals per se or communication media.

According to various configurations, the computer 700 can operate in a networked environment using logical connections to a remote computer(s) 724 through a network 720. For example, if the computer 700 corresponds to a computing device 116 that determines is a polynucleotide taggant 100 is authentic then the remote computer 724 may correspond to the user device 124 that displays the results of the determination. The network 720 may also provide a connection to a capture device 114 that captures a detected pattern from a substrate. The computer 700 can connect to the network 720 through a network interface unit 722 connected to the bus 710. It should be appreciated that the network interface unit 722 can also be utilized to connect to other types of networks and remote computer systems. The computer 700 can also include an input/output controller 718 for receiving and processing input from a number of other devices, including a keyboard, mouse, touch input, and an electronic stylus (not shown). Similarly, the input/output controller 718 can provide output to a display screen or other type of output device (not shown).

It should be appreciated that the software components described herein, when loaded into the processing unit(s) 702 and executed, can transform the processing unit(s) 702 and the overall computer 700 from a general-purpose computing device into a special-purpose computing device customized to facilitate the functionality presented herein. The processing unit(s) 702 can be constructed from any number of transistors or other discrete circuit elements, which can individually or collectively assume any number of states. More specifically, the processing unit(s) 702 can operate as a finite-state machine, in response to executable instructions contained within the software modules disclosed herein. These computer-executable instructions can transform the processing unit(s) 702 by specifying how the processing unit(s) 702 transitions between states, thereby transforming the transistors or other discrete hardware elements constituting the processing unit(s) 702.

Encoding software modules can also transform the physical structure of the computer-readable media presented herein. The specific transformation of physical structure depends on various factors, in different implementations of this description. Examples of such factors include, but are not limited to, the technology used to implement the computer-readable media, whether the computer-readable media is characterized as primary or secondary storage, and the like. For example, if the computer-readable media is implemented as semiconductor-based memory, the software disclosed herein can be encoded on the computer-readable media by transforming the physical state of the semiconductor memory. For instance, the software can transform the state of transistors, capacitors, or other discrete circuit elements constituting the semiconductor memory. The software can also transform the physical state of such components to store data thereupon.

As another example, the computer-readable media disclosed herein can be implemented using magnetic or optical technology. In such implementations, the software presented herein can transform the physical state of magnetic or optical media, when the software is encoded therein. These transformations can include altering the magnetic characteristics of particular locations within given magnetic media. These transformations can also include altering the physical features or characteristics of particular locations within given optical media, to change the optical characteristics of those locations. Other transformations of physical media are possible without departing from the scope and spirit of the present description, with the foregoing examples provided only to facilitate this discussion.

In light of the above, it should be appreciated that many types of physical transformations take place in the computer 700 to store and execute software components and functionalities presented herein. It also should be appreciated that the architecture shown in FIG. 7 for the computer 700, or a similar architecture, can be utilized to implement many types of computing devices such as desktop computers, notebook computers, servers, supercomputers, gaming devices, tablet computers, and other types of computing devices known to those skilled in the art. It is also contemplated that the computer 700 might not include all of the components shown in FIG. 7, can include other components that are not explicitly shown in FIG. 7, or can utilize an architecture completely different than that shown in FIG. 7.

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments described herein may be combined together unless context clearly indicates otherwise. As used herein in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. This clause provides and example of a method that may be performed by a user to determine if an item is authentic.

A method of authenticating an item (102) comprising:
collecting a polynucleotide taggant (100) from the item, wherein the polynucleotide taggant comprises a plurality of synthetic polynucleotides (104) that collectively encode a bit sequence (300) using the sequences of the polynucleotides and hybridization states of the polynucleotides;
contacting a substrate (106) with the polynucleotide taggant under conditions suitable for polynucleotide hybridization, wherein bound polynucleotide complexes (200) on the substrate hybridize with and emit a detectable pattern (112) based on the bit values of the synthetic polynucleotides, wherein the substrate detects only a subset of bits in the bit sequence encoded by the polynucleotide taggant;
capturing the detectable pattern and a validation code (110) associated with the substrate;
sending the detectable pattern and the validation code to a computing device (116), wherein the computing device determines a correct pattern based on the validation code and performs a comparison of the detectable pattern to the correct pattern;
receiving from the computing device a determination of the item as authentic or not authentic based on the comparison; and
rendering a result of the determination.

Clause 2. The method of clause 1, wherein the substrate is one of a plurality of substrates that each validate the polynucleotide taggant and each detect a different subset of bits in the bit sequence encoded by the polynucleotide taggant.

Clause 3. The method of any of clauses 1 or 2, wherein the bound polynucleotide complexes detect bit values of the polynucleotide taggant by hybridization to the synthetic polynucleotides and participation in deoxyribonucleic acid strand displacement (DSD) reactions that result in displacement of strands of the bound polynucleotide complexes.

Clause 4. The method of any of clauses 1 to 3, wherein the detectable pattern is a change in a signal resulting from displacement of reporter molecules bound to the substrate or attachment of reporter molecules to the substrate.

Clause 5. The method of any of clauses 1 to 4, wherein the validation code is unique to the substrate and provides information to identify the correct pattern for that substrate.

Clause 6. The method of any of clauses 1 to 5, wherein the synthetic polynucleotides encode, for each bit in the bit sequence, either a first bit value by a single-stranded synthetic polynucleotide or a second bit value by the single-stranded synthetic polynucleotide hybridized to a blocker strand.

Clause 7. This clause provides an example of a system that includes the tag, the ticket, and the cloud system.

A system for authenticating an item (102) comprising:
- a polynucleotide taggant (100) comprising a plurality of synthetic polynucleotides (104) that collectively encode a bit sequence (300) using the sequences of the polynucleotides and hybridization states of the polynucleotides;
- a plurality of substrates (106) each comprising a plurality of bound polynucleotide complexes (200) attached to the substrates, wherein the bound polynucleotide complexes on each substrate are configured to detect a different bit subset (504) of the bit sequence encoded by the polynucleotide taggant by hybridization to the synthetic polynucleotides and emission of a detectable pattern (112) based on the bit subset detected by the substrate, and wherein each one of the substrates is associated with a validation code (110); and
- a computing device (116) configured to, for a one of the plurality of substrates, receive the detectable pattern and the validation code, determine a correct pattern (118) based on the validation code, and perform a comparison of the detectable pattern to the correct pattern.

Clause 8. The system of clause 7, wherein the polynucleotide taggant encodes, for each bit in the bit sequence, either a first bit value by a single-stranded synthetic polynucleotide or a second bit value by the single-stranded synthetic polynucleotide hybridized to a blocker strand.

Clause 9. The system of clause 7 or 8, wherein the bound polynucleotide complexes are configured to detect bit values of the polynucleotide taggant by hybridization to the synthetic polynucleotides and participation in DSD reactions that result in displacement of strands of the bound polynucleotide complexes.

Clause 10. The system of any of clauses 7 to 9, wherein the strands of the bound polynucleotide complexes that are displaced include reporter molecules and the detectable pattern is a pattern of decrease of signal or wherein the synthetic polynucleotides include reporter molecules and the detectable pattern is a pattern of increase of signal.

Clause 11. The system of any of clauses 7 to 10, wherein the computing device is further configured to decode the bit subset using an encoding scheme to recover the bit sequence.

Clause 12. The system of any of clauses 7 to 11, wherein each of the plurality of substrates is associated with a unique validation code.

Clause 13. The system of clause 12, wherein the computing device is configured to return an indication of not authentic or an error if a same validation code is received more than once.

Clause 14. The system of any clauses 7 to 13, further comprising a user device configured to render a determination of the item as authentic or not authentic based on the comparison.

Clause 15. This clause provides one example of a method of preparing a set of tickets that each detect a different set of bits.

A method of manufacturing a plurality of substrates (106) to use for authenticating an item (102) comprising:
- generating on each of the plurality of substrates a plurality of physically separated assay locations (108);
- synthesizing a plurality of bound polynucleotide complexes (200) that each comprise a bound strand (202) configured to attach to one of the assay locations and a reporter strand (204) configured to hybridize to the bound strand, wherein one of the bound strand or the reporter strand includes a toehold domain (210) that does not hybridize to the other strand and wherein each of the bound polynucleotide complexes includes a unique barcode domain (206) indicating a specific bit position (302) in a bit sequence (300); and
- binding individual ones of the bound polynucleotide complexes to assay locations on the plurality of substrates such that at each individual assay location all the bound polynucleotide complexes have the same unique barcode domain and that a pattern of which unique barcode domains are bound at the assay locations is different for each substrate in the plurality of substrates.

Clause 16. The method of clause 15, wherein the substrates are nitrocellulose membranes and generating a plurality of physically separated assay locations comprises depositing a pattern of hydrophobic barriers with a wax-based printer.

Clause 17. The method of clause 15 or 16, wherein the plurality of physically separated assay locations includes at least nine separate assay locations on each substrate.

Clause 18. The method of any of clauses 15 to 17, wherein synthesizing the plurality of bound polynucleotide complexes comprises synthesizing each bound strand and each reporter strand followed by pre-hybridizing bound strands and reporter strands having the same unique barcode domain.

Clause 19. The method of any of clauses 15 to 18, wherein synthesizing the reporter strand comprises attaching a reporter molecule to the reporter strand.

Clause 20. The method of any of clauses 15 to 19, further comprising, incubating one of the substrates with a solution that contains a polynucleotide taggant, wherein the polynucleotide taggant comprises a plurality of synthetic polynucleotides that collectively encode a bit sequence using the sequences of the polynucleotides and hybridization states of the polynucleotides, wherein the one of the substrates detects only a subset of bits in the bit sequence encoded by the polynucleotide taggant.

CONCLUSION

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The terms "a," "an," "the" and similar referents used in the context of describing the invention are to be construed to cover both the singular and the plural unless otherwise indicated herein or clearly contradicted by context. The terms "based on," "based upon," and similar referents are to be construed as meaning "based at least in part" which includes being "based in part" and "based in whole," unless otherwise indicated or clearly contradicted by context. The terms "portion," "part," or similar referents are to be construed as meaning at least a portion or part of the whole including up to the entire noun referenced. As used herein, "approximately" or "about" or similar referents denote a range of ±10% of the stated value.

For ease of understanding, the processes discussed in this disclosure are delineated as separate operations represented as independent blocks. However, these separately delineated operations should not be construed as necessarily order-dependent in their performance. The order in which the processes are described is not intended to be construed as a limitation, and unless other otherwise contradicted by context any number of the described process blocks may be combined in any order to implement the process or an alternate process. Moreover, it is also possible that one or more of the provided operations is modified or omitted.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents and/or patent applications throughout this specification. Each of the cited references is individually incorporated herein by reference for its particular cited teachings as well as for all that it discloses.

The invention claimed is:

1. A method of authenticating an item comprising:
   collecting a polynucleotide taggant from the item, wherein the polynucleotide taggant comprises a plurality of synthetic polynucleotides that collectively encode a bit sequence using sequences of the polynucleotides and hybridization states of the polynucleotides;
   contacting a substrate with the polynucleotide taggant under conditions suitable for polynucleotide hybridization, wherein bound polynucleotide complexes on the substrate hybridize with and emit a detectable pattern based on bit values of the synthetic polynucleotides, wherein the substrate detects only a subset of bits in the bit sequence encoded by the polynucleotide taggant;
   capturing the detectable pattern and a validation code associated with the substrate;
   sending the detectable pattern and the validation code to a computing device wherein the computing device determines a correct pattern based on the validation code and performs a comparison of the detectable pattern to the correct pattern; and
   receiving from the computing device a determination of the item as authentic or not authentic based on the comparison.

2. The method of claim 1, wherein the substrate is one of a plurality of substrates that each validate the polynucleotide taggant and each detect a different subset of bits in the bit sequence encoded by the polynucleotide taggant.

3. The method of claim 1, wherein the bound polynucleotide complexes detect bit values of the polynucleotide taggant by hybridization to the synthetic polynucleotides and participation in deoxyribonucleic acid strand displacement (DSD) reactions that result in displacement of strands of the bound polynucleotide complexes.

4. The method of claim 1, wherein the detectable pattern is a change in a signal resulting from displacement of reporter molecules bound to the substrate or attachment of reporter molecules to the substrate.

5. The method of claim 1, wherein the validation code is unique to the substrate and provides information to identify the correct pattern for that substrate.

6. The method of claim 1, wherein the synthetic polynucleotides encode, for each bit in the bit sequence, either a first bit value by a single-stranded synthetic polynucleotide or a second bit value by the single-stranded synthetic polynucleotide hybridized to a blocker strand.

7. The method of claim 1, further comprising rendering a result of the determination.

8. A system for authenticating an item comprising:
   a polynucleotide taggant comprising a plurality of synthetic polynucleotides that collectively encode a bit sequence using sequences of the polynucleotides and hybridization states of the polynucleotides; and
   a plurality of substrates each comprising a plurality of bound polynucleotide complexes attached to the substrates, wherein the bound polynucleotide complexes on each substrate are configured to detect a different bit subset of the bit sequence encoded by the polynucleotide taggant by hybridization to the synthetic polynucleotides and emission of a detectable pattern based on the bit subset detected by the substrate, and wherein each one of the substrates is associated with a validation code configured to, for a one of the plurality of substrates, receive the detectable pattern and the validation code, determine a correct pattern based on the validation code, and perform a comparison of the detectable pattern to the correct pattern.

9. The system of claim 8, wherein the polynucleotide taggant encodes, for each bit in the bit sequence, either a first bit value by a single-stranded synthetic polynucleotide or a second bit value by the single-stranded synthetic polynucleotide hybridized to a blocker strand.

10. The system of claim 8, wherein the bound polynucleotide complexes are configured to detect bit values of the polynucleotide taggant by hybridization to the synthetic polynucleotides and participation in DSD reactions that result in displacement of strands of the bound polynucleotide complexes.

11. The system of claim 10, wherein the strands of the bound polynucleotide complexes that are displaced include reporter molecules and the detectable pattern is a pattern of decrease of signal.

12. The system of claim 10, wherein the synthetic polynucleotides include reporter molecules and the detectable pattern is a pattern of increase of signal.

13. The system of claim 8, further comprising a computing device, wherein the computing device is configured to decode the bit subset using an encoding scheme to recover the bit sequence.

14. The system of claim 8, wherein each of the plurality of substrates is associated with a unique validation code.

15. The system of claim 14, further comprising a computing device, wherein the computing device is configured to return an indication of not authentic or an error if a same validation code is received more than once.

16. The system of claim 8, further comprising a user device configured to render a determination of the item as authentic or not authentic based on the comparison.

17. The system of claim 8, wherein the substrates are nitrocellulose membranes having a plurality of physically separated assay locations.

18. The system of claim 17, wherein the plurality of physically separated assay locations includes at least nine separate assay locations on each substrate.

19. The system of claim 8, wherein the validation code is a string of human-readable letters or numbers, a barcode, or a quick-response (QR) code.

20. The system of claim 19, wherein the validation code is physically attached to the substrate.

\* \* \* \* \*